(12) United States Patent
Keyt

(10) Patent No.: US 8,557,761 B2
(45) Date of Patent: Oct. 15, 2013

(54) INFUSED SEALANT SYSTEM

(76) Inventor: Kathryn L. Keyt, Folsom, CA (US)

(*) Notice: Subject to any disclaimer, the term of this patent is extended or adjusted under 35 U.S.C. 154(b) by 622 days.

(21) Appl. No.: 12/017,252

(22) Filed: Jan. 21, 2008

(65) Prior Publication Data

US 2009/0111729 A1   Apr. 30, 2009

Related U.S. Application Data

(60) Provisional application No. 60/918,484, filed on Mar. 16, 2007.

(51) Int. Cl.
*A61K 8/00* (2006.01)
*A61K 8/18* (2006.01)
*A61K 8/02* (2006.01)
*A61Q 13/00* (2006.01)
*C11B 9/00* (2006.01)
*C11B 9/02* (2006.01)
*C08K 11/00* (2006.01)
*C08L 91/06* (2006.01)
*C04B 24/08* (2006.01)

(52) U.S. Cl.
USPC ............ 512/1; 512/5; 523/129; 424/401; 260/22; 106/230; 106/610; 106/620

(58) Field of Classification Search
USPC ........... 424/401; 512/1, 5; 260/22; 523/129; 106/230, 610, 620
See application file for complete search history.

(56) References Cited

U.S. PATENT DOCUMENTS

| | | | | |
|---|---|---|---|---|
| 1,415,282 A * | 5/1922 | Walsh | | 106/610 |
| 4,072,785 A * | 2/1978 | Taylor et al. | | 428/536 |
| 4,110,281 A * | 8/1978 | Dreer | | 523/129 |
| 4,361,659 A | 11/1982 | Friedemann | | |
| 4,640,690 A * | 2/1987 | Baumgartner et al. | | 8/506 |
| 4,994,509 A | 2/1991 | Laurent | | |
| 5,102,741 A * | 4/1992 | Miyabayashi | | 428/447 |
| 2001/0007676 A1* | 7/2001 | Mui et al. | | 424/401 |
| 2003/0077238 A1 | 4/2003 | Roovers | | |
| 2003/0108743 A1* | 6/2003 | Anderson | | 428/402.24 |
| 2003/0147838 A1* | 8/2003 | Amato et al. | | 424/70.17 |
| 2004/0057924 A1 | 3/2004 | Gustavsson | | |
| 2004/0223931 A1 | 11/2004 | Mondet | | |
| 2004/0266302 A1 | 12/2004 | DiSalvo | | |
| 2006/0005742 A1 | 1/2006 | Moeschl | | |
| 2006/0129179 A1* | 6/2006 | Weber et al. | | 606/194 |
| 2006/0191290 A1 | 8/2006 | Chesne | | |

FOREIGN PATENT DOCUMENTS

| | | | | |
|---|---|---|---|---|
| JP | 63022336 | * | 1/1988 | ............ C08J 5/00 |
| JP | 2004-026656 | * | 1/2004 | ............ A61K 8/18 |
| JP | 2004105244 | | 4/2004 | |
| WO | WO2006026168 | | 3/2006 | |

OTHER PUBLICATIONS

Pritchard, G. "Novel and Traditional Fillers for Plastics", {Publisher: Rapra 1999 p. 63 ISBN-9781859571835}.*
Silica fume Wikipedia {http://en.wikipedia.org/wiki/silica_fum}.*
Ornitz: All About Rope 6th paragraph (www.mapability.com/ei8ic/contest/rope.php).*
Camphor Esoteric Oils Product data {http://www.essentialoils.co.za/camphor.htm}.*
Smallest Particle Size Seen Answers.com Mar. 9, 2010 {http://wiki.answers.com/Q/What_is_the_smallest_particle_size_that_can_be_seen_with_the_naked_human_eye}.*
The Free Dictionary (Molded entry—corresponding per American Heritage Dictionary of the English Language © 2000 taken as Dec. {http://www.thefreedictionary.com/molded}.*
The Engineering Tool Box {http://www.engineeringtoolbox.com/particle-sizes-d_934.html} (Wayback Verification Crawl presence date Mar. 14, 2006.*
Roget's International Thesaurus of English Words and Phrases {New York, Crowell Company 1922}).*
Kydd et al. (Journal of Prostetic Denstistry Jan. 1996 pp. 9-13).*
Fisher Scientific MSDS (Quartz MSDS 2006 Jan. 18 {http://avogadro.chem.iastate.edu/MSDS/sand.htm}).*
Mary Schimpff (see Mary Schimpff Home page {http://www.modernsilver.com/schimpff.htm} Copyright 2003 [Taken as Dec.]).*
Cerne MSDS (Ground Limestone MSDS Aug. 2006) DesMoines IA USA.*
Ding Fundamental Theory of Transmission Electronic Microscopy {http://web.archive.org/web/20051023133534/http://www.nanoscience.gatech.edu/zlwang/research/tem.html}.*
Real Dictionary (Transparent entry; {http://www.realdictionary.com/?q=transparent} © 2001 Princeton University, Princeton NJ USA available May 26 2003).*
Gardner, Vibrational Healing Through the Chakras, 2006, pgs. 54-55, The Crossing Press.
Foley, Embraced by the Essence—Your Journey into Wellness Using Pure Quality Essential Oils, 2000, pg. 13, Komar Enterprises, LLC.
Hawkins, Power vs. Force: The Hidden Determinants of Human Behavior, 2002, pgs. 29-31, Hay House, Inc.
Highley, The Reference Guide for Essential Oils, 9th Ed., 2005, pgs. 1-4, Abundant Health.
Katz, Gemstone Energy Medicine: Healing Body, Mind and Spirit, 2005, pgs. 18-19, Gemisphere.
Skymall, Inc., Trion:Z Bracelet or Necklace, retrieved at http://www.skymall.com/shopping/search.htm on Feb. 1, 2008, 2 pgs.
Patent Cooperation Treaty, International Search Report and Written Opinion, Aug. 11, 2009, PCT/US2009/030566.

* cited by examiner

*Primary Examiner* — Patrick Ryan
*Assistant Examiner* — Aaron Greso

(57) ABSTRACT

An infused sealant system for providing a sealant infused with a crystal powder and/or essential oil. The infused sealant system generally includes a composition comprised of a sealant infused with a crystal powder. The composition preferably includes one or more essential oils infused within the sealant. The composition is applied as a coating or an adhesive to an object in a liquid state and allowed to dry thereby sealing the crystal powder and/or essential oils within the sealant.

16 Claims, No Drawings

INFUSED SEALANT SYSTEM

CROSS REFERENCE TO RELATED APPLICATIONS

I hereby claim benefit under Title 35, United States Code, Section 119(e) of U.S. provisional patent application Ser. No. 60/918,484 filed Mar. 16, 2007. The 60/918,484 application is currently pending. The 60/918,484 application is hereby incorporated by reference into this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to sealants for coating objects and more specifically it relates to an infused sealant system for providing a sealant infused with a crystal powder and/or essential oil.

2. Description of the Related Art

Any discussion of the related art throughout the specification should in no way be considered as an admission that such related art is widely known or forms part of common general knowledge in the field.

Crystals (e.g. quartz crystal) and essential oils (e.g. ginger oil) have been in use for years by individuals that want to enjoy the benefits of having the same near them. Crystals are used today by individuals for various intended purposes including the practice of feng shui. Essential oils are used today by individuals for various intended purposes including but not limited to aroma therapy and the practice of feng shui. U.S. Pat. No. 5,805,768 titled Aroma Therapy Diffuser discloses an exemplary aroma therapy diffuser.

The main problem with conventional crystal is that they must be placed upon an upper surface to be exposed resulting in the loss of surface space. In addition, the crystal may be considered aesthetically unpleasing by some individuals particularly when placed on a surface within a home. Another problem with conventional crystal is that they can become stolen, removed, misplaced or lost requiring the purchase of additional crystal.

The main problem with essential oils is that once they are exposed to air they immediately start to evaporate until only dry components remain for the essential oils. Another problem with essential oils is that they must be retained within a container which consumes space and can be aesthetically unpleasing by some individuals. In addition, essential oils maintained within a container are susceptible to accidental spillage or evaporation. A further problem with essential oils is that they can be costly to replace.

Because of the inherent problems with the related art, there is a need for a new and improved infused sealant system for providing a sealant infused with a crystal powder and/or essential oil.

BRIEF SUMMARY OF THE INVENTION

The invention generally relates to a sealant which includes a composition comprised of a sealant infused with a crystal powder. The composition preferably includes one or more essential oils infused within the sealant. The composition is applied as a coating or an adhesive to an object in a liquid state and allowed to dry thereby sealing the crystal powder and/or essential oils within the sealant.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the composition or system set forth in the following description. The invention is capable of other embodiments and of being practiced and carried out in various ways. Also, it is to be understood that the phraseology and terminology employed herein are for the purpose of the description and should not be regarded as limiting.

An object is to provide an infused sealant system for providing a sealant infused with a crystal powder and/or essential oil.

Another object is to provide an infused sealant system that is capable of coating and/or securing various types of objects.

An additional object is to provide an infused sealant system that eliminates the need to place large pieces of crystal on a surface.

A further object is to provide an infused sealant system that provides an aesthetically pleasing system to present crystal and/or essential oils within a building.

Another object is to provide an infused sealant system that eliminates the risk of theft, removal, misplacement or loss of valuable crystal.

Another object is to provide an infused sealant system that maintains one or more essential oils in a liquid state.

Another object is to provide an infused sealant system that eliminates the need to store essential oils within a container.

Another object is to provide an infused sealant system that eliminates the risk of accidental spillage or evaporation of essential oils.

Other objects and advantages of the present invention will become obvious to the reader and it is intended that these objects and advantages are within the scope of the present invention.

DETAILED DESCRIPTION OF THE INVENTION

A. Overview.

The present invention comprises a composition comprised of a sealant infused with a crystal powder. The composition preferably includes one or more essential oils infused within the sealant. The composition is applied as a coating or an adhesive to an object in a liquid state and allowed to dry thereby sealing the crystal powder and/or essential oils within the sealant.

B. Sealant.

The present invention includes a volume of sealant. The sealant is initially in a liquid state and is capable of being applied to an object as a coating and an adhesive. The sealant in the liquid state may also be molded, formed or shaped as may be desired. The sealant preferably enters a solid state when exposed to air after being applied to an object. The sealant is comprised of a durable material to last a significant amount of time when attached to an object.

The sealant is preferably comprised of a substantially transparent material to not interfere with the appearance of the object applied to. The sealant may be comprised of a semi-transparent material. The sealant may also be colored to correspond to the color of the object applied to. The sealant may also be colored for use in painting an object to a desired color.

The sealant may be comprised of various types of coatings and adhesives such as but not limited to a gloss, a lacquer, a nail polish, a varnish, a paint, glue, rubber cement, epoxy, silicone, lotion, wax, cream and the like. Once the sealant is applied to the object being coated, the sealant changes to a solid state and remains attached to the object in a durable manner.

C. Crystal Powder.

A volume of crystal powder is infused within the sealant. The crystal powder is preferably comprised of a crystal ground into a fine powder state that mixes within the sealant. The crystal powder preferably is ground fine enough so that when the crystal powder is mixed with the sealant the crystal powder is not visible within the sealant. The crystal powder is preferably substantially transparent to decrease the visibility within the sealant.

The crystal powder may be comprised of natural crystal or synthetic crystal. The crystal powder is preferably comprised of quartz crystal, however other types of crystal may be used to make the crystal powder.

The crystal powder may be manufactured using various types of powderizing systems. The crystal powder may be comprised of one or more crystal materials combined together. The crystal powder may be infused within the sealant within an essential oil or without an essential oil.

D. Essential Oil.

At least one essential oil is preferably infused within the sealant. The essential oil may be infused within the sealant with the crystal powder or without the crystal powder. The essential oil is substantially encapsulated within the sealant in both the liquid state and in the solid state of the sealant.

When the sealant enters the solid state after being applied to an object, the essential oil remains substantially in a liquid state within the sealant in a sealed manner and does not evaporate. When the essential oil is encapsulated within the sealant, there is no evaporation or scent emitted from the solidified sealant. The encapsulated essential oil remains within the sealant for long period of time.

E. Kit.

The present invention may be incorporated into a kit comprised of an openable container having a plurality of vials each containing a different composition of the present invention. A brush or other applicator may also be included within the kit to apply the composition to an object.

F. Usage of Composition.

The composition may be applied to various objects such as but not limited to gemstones, walls, floors, furniture, doors, baseboards, door trim, vehicles, boats, countertops, appliances, cell phones, personal digital assistants, picture frames, finger nails, jewelry, patches and the like. The composition may be applied as a coating for the outer surface of the object or as an adhesive to secure the object to another object.

What has been described and illustrated herein is a preferred embodiment of the invention along with some of its variations. The terms, descriptions and figures used herein are set forth by way of illustration only and are not meant as limitations. Those skilled in the art will recognize that many variations are possible within the spirit and scope of the invention, which is intended to be defined by the following claims (and their equivalents) in which all terms are meant in their broadest reasonable sense unless otherwise indicated. Any headings utilized within the description are for convenience only and have no legal or limiting effect.

I claim:

1. An object coated with a sealant composition, comprising:
   an object;
   a sealant applied to said object as a coating and an adhesive;
   wherein said sealant is in a liquid state and where said sealant enters a solid state when exposed to air;
   a crystal powder within said sealant, wherein said crystal powder is substantially transparent, wherein said crystal powder has a particle size that is not visible within said sealant;
   an essential oil comprises a component in said sealant in a sealed manner within said sealant there is no evaporation of said essential oil from said sealant when in said solid state; and
   wherein said object is not a container for holding essential oil.

2. The object coated with a sealant composition of claim 1, wherein said sealant is substantially transparent.

3. The object coated with a sealant composition of claim 1, wherein said sealant is capable of being molded.

4. The object coated with a sealant composition of claim 1, wherein said sealant is comprised of a color which matches the color of said object.

5. The object coated with a sealant composition of claim 1, wherein said crystal powder is comprised of quartz crystal.

6. The object coated with a sealant composition of claim 1, wherein said composition includes an essential oil infused within said sealant.

7. The object coated with a sealant composition of claim 1, wherein said object is comprised of a gemstone.

8. The object coated with a sealant composition of claim 1, wherein said object is comprised of a wall.

9. The object coated with a sealant composition of claim 1, wherein said object is comprised of a floor.

10. The object coated with a sealant composition of claim 1, wherein said object is comprised of furniture.

11. The object coated with a sealant composition of claim 1, wherein said object is comprised of a vehicle.

12. The object coated with a sealant composition of claim 1, wherein said object is comprised of a cell phone.

13. The object coated with a sealant composition of claim 1, wherein said object is comprised of a countertop.

14. The object coated with a sealant composition of claim 1, wherein said object is comprised of a picture frame.

15. The object coated with a sealant composition of claim 1, wherein said crystal powder is comprised of natural crystal.

16. The object coated with a sealant composition of claim 1, wherein said crystal powder is comprised of synthetic crystal.

\* \* \* \* \*